United States Patent [19]
Jones et al.

[11] Patent Number: 5,714,447
[45] Date of Patent: Feb. 3, 1998

[54] DEODORANT SOAP OR DETERGENT COMPOSITION CONTAINING A ZINC COMPOUND AND A POLYAMINE

[75] Inventors: Keith A. Jones, Lambertville, N.J.; Todd W. Domke, Newtown, Pa.; Janet Gardella, Howell, N.J.

[73] Assignee: Church & Dwight Co., Inc., Princeton, N.J.

[21] Appl. No.: 590,736

[22] Filed: Jan. 24, 1996

[51] Int. Cl.$^6$ ................................ C11D 9/00; C11D 3/37
[52] U.S. Cl. .................. 510/131; 510/130; 510/133; 510/499
[58] Field of Search ...................... 510/130, 131, 510/133, 122, 499, 127

[56] References Cited

U.S. PATENT DOCUMENTS

| | | | |
|---|---|---|---|
| 4,022,880 | 5/1977 | Vinson et al. | 424/49 |
| 4,082,841 | 4/1978 | Pader | 424/50 |
| 4,275,054 | 6/1981 | Sebag et al. | 424/65 |
| 4,322,308 | 3/1982 | Hooper et al. | 252/107 |
| 4,522,806 | 6/1985 | Muhlemann et al. | 424/52 |
| 4,933,101 | 6/1990 | Cilley et al. | 252/99 |
| 5,000,870 | 3/1991 | Shimizu | 252/183.11 |
| 5,403,506 | 4/1995 | Jones | 252/108 |
| 5,573,699 | 11/1996 | Jones et al. | 510/131 |
| 5,576,279 | 11/1996 | Pyles | 510/122 |

*Primary Examiner*—Paul Lieberman
*Assistant Examiner*—Necholas Ogden
*Attorney, Agent, or Firm*—Irving Fishman

[57] ABSTRACT

A deodorant soap or detergent composition comprising a surfactant, e.g., a soap or synthetic detergent, and either 1) minor but effective amounts in uncomplexed form of a water-insoluble zinc compound, e.g., zinc oxide, and a water-soluble zinc-complexing polyamine which is a polyalkyleneamine or a basic aminoacid polymer; or 2) a water-soluble complex of said water-insoluble zinc compound and said water-soluble zinc-complexing polyamine.

17 Claims, No Drawings

DEODORANT SOAP OR DETERGENT COMPOSITION CONTAINING A ZINC COMPOUND AND A POLYAMINE

BACKGROUND OF THE INVENTION

1. Field of the Invention

The invention relates to a novel deodorant toilet soap or detergent composition.

2. Background Information Including Description of Related Art

Perspiration produced directly by the sweat glands of the body are generally odorless or have an innocuous odor. However, unpleasant body odors are often caused by the breakdown of the components of such perspiration by bacteria to produce foul-smelling substances such as butyric acid. Thus, deodorant detergent compositions, e.g., soaps, have been developed containing any of various additives known to act as bactericides or bacteriostats in order to keep the bacteria population on the skin low and hence minimize the breakdown of the perspiration components. It has been found, however, that the most widely used of these additives have certain disadvantages. For example, hexachlorophene which was extensively used as a deodorizing additive for several years, has been shown to have a degree of neurotoxicity causing the U.S. Food and Drug Administration to prohibit its use unless prescribed by a physician. Triclocarban (3,4,4'-trichlorocarbanilide), which is presently used in many deodorant soaps, has been found to be a skin irritant in some instances. Thus, any deodorant detergent composition which does not have these disadvantages would be highly desirable.

The following references may be considered material to the invention.

U.S. Pat. No. 4,022,880, issued May 10, 1977 to Vinson et al., discloses oral compositions for inhibiting plaque and calculus formation comprising a zinc compound, an antibacterial agent which may be a nitrogen compound such as a chlorhexedine, and a polishing agent such as a polymerized melamine, e.g., melamine-formaldehyde resin.

U.S. Pat. No. 4,082,841, issued Apr. 4, 1978 to Pader, teaches an oral composition for reducing dental plaque and calculus formation comprising zinc ions, an antibacterial agent which may be neomycin sulfate and a bodying agent which may be polyvinylpyrrolidone.

U.S. Pat. No. 4,322,308, issued Mar. 30, 1982 to Hooper et al., discloses a deodorant detergent composition comprising a detergent active compound, a deodorant perfume, and a deodorant other than a deodorant perfume, which may be a zinc "salt" such as zinc oxide.

U.S. Pat. No. 4,522,806, issued Jun. 11, 1985 to Muhlemann et al., discloses oral compositions which inhibit the formation of dental plaque and calculus, comprising an antibacterial pyrimidine amine base, e.g., hexetidine, and a zinc salt.

U.S. Pat. No. 4,933,101, issued Jun. 12, 1990 to Cilley et al., disclose liquid automatic dishwashing compositions containing an insoluble inorganic zinc "salt", e.g., zinc oxide, useful for inhibition of glassware corrosion.

U.S. Pat. No. 5,000,870, issued Mar. 19, 1991 to Shimizu, discloses a process for converting waste cooking oil to a soap or detergent by cooking the oil with a substance comprising an alkali metal carbonate such as sodium bicarbonate and a component having deodorization capabilities such as zinc oxide.

Application Ser. No. 08/269,055, filed Jun. 30, 1994, discloses aqueous zinc-polyamine complex solutions. The entire disclosure relating to the nature of the complex solution and its method of preparation is incorporated herein by reference.

Application Ser. No. 08/280,411, filed Jul. 26, 1994, discloses dentifrices containing a zinc-polyamine complex. The entire disclosure relating to the nature of the complex and its method of preparation is incorporated herein by reference.

SUMMARY OF THE INVENTION

In accordance with the invention, a deodorant soap or detergent composition is provided comprising a surfactant, e.g., a soap or synthetic detergent, and as a deodorizing component, either 1) minor but effective amounts in uncomplexed form of a water-insoluble zinc compound and a water-soluble zinc-complexing polyamine which is a polyalkyleneamine or an aminoacid polymer; or 2) a water-soluble complex of said water-insoluble zinc compound and said water-soluble zinc-complexing polyamine. The composition is particularly useful as a personal toilet soap or detergent composition.

DETAILED DESCRIPTION OF THE INVENTION

The soap and detergent compositions of this invention are solid or liquid and comprise a surface active or surfactant component, e.g., a soap or synthetic detergent, which contains a relatively polar hydrophilic group and a relatively non-polar hydrophobic group. The soaps are salts of relatively long chain fatty acids having the formula R—COO$^-$ X$^+$, where R is often an unbranched saturated or unsaturated aliphatic group but may contain branches or even ring groups. Thus, the carboxylate (—COO$^-$) groups constitute the hydrophilic groups of the soap molecule while the long carbon chain R groups constitute the hydrophobic groups. In order for the soap to have adequate solubility in water, the cation of the soap, X$^+$, is usually an alkali metal, e.g., sodium or potassium, or, more rarely, an ammonium or substituted ammonium group.

Typical soaps contemplated under this invention are the water-soluble alkali metal, e.g., potassium and sodium, soaps of the saturated and unsaturated higher fatty acids having from about eight to about twenty-six carbon atoms, such as capric, caprylic, lauric, myristic, palmitic, stearic, oleic, linoleic, linolenic, arachidic, behenic, margaric, tridechoic, and cerotic acids and the mixtures of such acids naturally occurring in fats, oils, waxes and rosins, such as the soaps of coconut oil fatty acids, tallow fatty acids, pig fat, fish oil fatty acids, beeswax, palm oil fatty acids, sesame oil fatty acids, peanut oil fatty acids, olive oil fatty acids, palm kernel oil fatty acids, cottonseed oil fatty acids, soybean oil fatty acids, corn oil fatty acids, babassu oil fatty acids, rosin acids, abietic acid and greases.

Solid soaps generally comprise a predominantly sodium salt of longer chain and/or more saturated carboxylic acids present in a composition containing a relatively small amount of water. In contrast, the surfactant of a liquid soap often contains a substantial proportion of potassium and/or ammonium cations in place of or in addition to sodium ions. Moreover such liquid soap surfactant is usually a salt of a shorter chain and/or more unsaturated carboxylic acid, and is mixed with a larger percentage of water.

The synthetic detergents contemplated as surfactants under this invention are compounds other than soap whose detersive properties, like soap, are due to the presence of a hydrophilic and a hydrophobic group in the molecule.

However, unlike soaps, synthetic detergents are not salts of carboxylic acids derived from fats and oils. Rather, the hydrophilic portion of the surfactant of a synthetic detergent is generally derived from a compound containing a relatively long carbon chain, e.g., a hydrocarbon obtained from petroleum refining and/or olefin polymerization or a long chain fatty acid, while the hydrophilic portion is the result of chemical modification of such compound to introduce the desired polar group, e.g., a hydroxyl, sulfate or sulfonate group.

The synthetic detergent compositions of this invention generally contain at least one anionic or nonionic surfactant or a mixture of the two types of surfactant.

The contemplated water soluble anionic detergent surfactants are the alkali metal (such as sodium and potassium) salts of the higher linear alkyl benzene sulfonates and the alkali metal salts of sulfated ethoxylated and unethoxylated fatty alcohols, and ethoxylated alkyl phenols. The particular salt will be suitably selected depending upon the particular formulation and the proportions therein.

The sodium alkybenzenesulfonate surfactant (LAS) most preferably used in the composition of the present invention has a straight chain alkyl radical of average length of about 11 to 13 carbon atoms.

Specific sulfated surfactants which can be used in the compositions of the present invention include sulfated ethoxylated and unethoxylated fatty alcohols, preferably linear primary or secondary monohydric alcohols with $C_{10}-C_{18}$, preferably $C_{12}-C_{16}$, alkyl groups and, if ethoxylated, on average about 1–15, preferably 3–12 moles of ethylene oxide (EO) per mole of alcohol, and sulfated ethoxylated alkylphenols with $C_8-C_{16}$ alkyl groups, preferably $C_8-C_9$ alkyl groups, and on average from 4–12 moles of EO per mole of alkyl phenol.

The preferred class of sulfated ethoxylated surfactants are the sulfated ethoxylated linear alcohols, such as the $C_{12}-C_{16}$ alcohols ethoxylated with an average of from about 1 to about 12 moles of ethylene oxide. A most preferred sulfated ethoxylated detergent is made by sulfating a $C_{12}-C_{15}$ alcohol ethoxylated with 3 moles of ethylene oxide.

Specific nonionic surfactants which can be used in the compositions of the present invention include ethoxylated fatty alcohols, preferably linear primary or secondary monohydric alcohols with $C_{10}-C_{18}$, preferably $C_{12}-C_{16}$, alkyl groups and on average about 1–15, preferably 3–12 moles of ethylene oxide (EO) per mole of alcohol, and ethoxylated alkylphenols with $C_8-C_{16}$ alkyl groups, preferably $C_8-C_9$ alkyl groups, and on average about 4–12 moles of EO per mole of alkyl phenol.

The preferred class of nonionic surfactants compounds are the ethoxylated linear alcohols, such as the $C_{12}-C_{16}$ alcohols ethoxylated with an average of from about 1 to about 12 moles of ethylene oxide. A most preferred nonionic detergent is a $C_{12}-C_{15}$ alcohol ethoxylated with 3 moles of ethylene oxide.

Mixtures of the foregoing synthetic detergent type of surfactants, e.g., of anionic and nonionic, or of different specific anionic or nonionic surfactants, may be used to modify the detergency, lather characteristics, and other properties of the composition. For example, a mixture of different fatty alcohols of 12 to 15 carbon atoms may be ethoxylated, directly sulfated, or sulfated after ethoxylation, a fatty alcohol may be partially ethoxylated and sulfated, or an ethoxylated fatty acid may be partially sulfated to yield a mixture of anionic and nonionic surfactants or different specific anionic or nonionic surfactants.

The term "water-insoluble" as employed herein refers to a zinc-containing compound which has a solubility in water that is equivalent to less than about 0.5 gram of zinc ions in 100 milliliters of water at 25° C. The slight solubility of the zinc compound in water is sufficient to slow-release bioavailable zinc ions in an aqueous environment.

Zinc compounds having a solubility which provides less than about 0.5 gram of bioavailable zinc ions per 100 milliliters of water at 25° C., and which are suitable as a complexed or uncomplexed ingredient in the soap or detergent compositions of the invention, include zinc oxide, zinc silicate, zinc carbonate, zinc tetrafluoroborate, zinc citrate, zinc oxalate, zinc stearate, and the like.

Zinc oxide is the preferred water-insoluble zinc compound of the invention. All zinc oxides are suitable for this purpose including USP grade zinc oxide from Zinc Corporation of America (ZCA). Submicron zinc oxide is preferred, e.g., having a primary particle size range of about 0.005 to 0.5 micron. The most preferred zinc oxide is an agglomerated submicron primary particle size zinc oxide, suitably having an agglomerated size of about 1 to 10 microns.

Specific, but non-limiting examples of zinc oxides having submicron average primary particle sizes are available from Sachtleben Chemie under the trademark "SACHTOTEC", from Presperse Inc. under the trademark "Finex 25", and from SunSmart under the trademark "Z-Cote". The SACHTOTEC particles have an average particle size of about 0.20 micron, but the particle size can be as small as 0.005–0.015 micron; the agglomerated particle size is about 4 to 6.5 microns. The Finex 25 particles have a particle size of about 0.1–0.5 micron; the agglomerated particle size is about 4–5 microns. The Z-Cote particles have an average particle size of about 0.1–0.5 micron; the agglomerated particle size is about 1–5 microns.

The term "water-soluble" as employed herein refers to polyamines which have a solubility of at least about 2 grams per 100 milliliters of water at 25° C. One class of polyamines which are suitable as a complexed or uncomplexed ingredient in the soap or detergent compositions of the invention are polyalkyleneamines having a weight average molecular weight, for example, in the range of about 800–1,000,000. A preferred type of polyalkyleneamine is a polyalkyleneimine having the formula

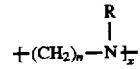

where R is a hydrogen, $C_1-C_3$ alkyl, or

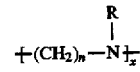

pe r 5substituent, n is an integer in the range of 2–6, and x has a value such that the compound has a weight average molecular weight in the range, for example, of about 800 to 1,000,000.

Another preferred type of polyamine which can be employed as a zinc-complexing ingredient in the compositions of the invention is a basic aminoacid polymer having a weight average molecular weight in the range, for example, of about 1500–70,000. Illustrative of these aminoacid polymers are polyarginine, polylysine and polyhistidine.

The water-insoluble zinc compound and zinc-complexing polyamine form a water-soluble complex when contacted with a sufficient amount of water. Thus, when added separately to soap or detergent compositions, the zinc compound and polyamine may form a water soluble complex in situ if sufficient water is present, e.g., in a bar or liquid soap or detergent composition. Alternatively, if desired for a specific purpose such as more efficient blending, an aqueous solution of a complex of the zinc compound and polyamine may be preformed by mixing the zinc compound and polyamine with a sufficient amount of water to facilitate the formation of the complex. For example, an aqueous solution of the complex can be prepared conveniently by dissolving the polyamine ingredient in an aqueous medium, and then adding the zinc compound in powder form to the aqueous solution with stirring to form the zinc-polyamine complex. Solubilizing of the zinc compound in the aqueous polyamine solution can also be facilitated by employing an ultrafine powder form. Zinc oxide having a submicron primary particle size and an average agglomerated particle size of from one to ten microns is a commercially available product sold under various trademarks as previously described.

After completion of the zinc compound addition, the resultant single-phase clear aqueous solution can have a pH above about 10 because of the polyamine basicity. Preferably, an acid reagent such as hydrochloric acid is added to adjust the aqueous solution pH into the range between about 6–10, since the basicity or acidity of solutions having a pH outside this range may result in irritation to the skin when the solution is incorporated into a toilet soap or detergent. The aqueous solution of the complex may then be blended with a solid or liquid surfactant, and, if desired, additional water and conventional adjuvants to form a solid or liquid deodorant soap or detergent composition.

In the case of soap or detergent compositions having either no water or too little water for the zinc compound and polyamine to form a complex, the zinc compound and polyamine may be employed in the composition in uncomplexed form since, when the composition is used in washing, sufficient water will be present to effect the formation of the water soluble complex. Whether utilized in the soap or detergent composition in complexed or uncomplexed form, the zinc compound and water-soluble zinc complexing polyamine ingredient may each be present in a relative amount, for example, of about 0.1–15 parts by weight, with the complex being formed if water is present in an amount, for example, of about 12–95 parts by weight. Note, however, that even if the zinc compound and polyamine are present in uncomplexed form, an acidic reagent, e.g., hydrochloric acid, should be employed if necessary to control the pH of a solution of the complex formed upon the addition of sufficient water, e.g., during washing, to between about 6 and 10 to avoid any semblance of skin irritation.

The finished soap or detergent composition whether solid or liquid, may contain for example about 1 to 25 wt. %, preferably about 5 to 15 wt. % of the zinc compound and polyamine in complexed or uncomplexed form, based on the weight of the total surfactant present in the composition.

The soap or detergent composition of this invention may also contain varying quantities of compatible adjuvants which do not materially interfere with the bactericidal effect of the zinc-polyamine complex. Typical of such compatible adjuvants are fillers and pigments such as titanium dioxide, diatomaceous earth, any of various colored pigments, dyes, fragrances, optical brighteners and bactericidal and bacteriostatic compounds other than the zinc-polyamine complex such as cetylpyridinium chloride.

The composition may be in solid form such as bars, flakes, chips, or powders or in liquid form. In addition to the possible differences discussed previously in the chemical nature of the active fatty acid salt in solid and liquid soap compositions, solid detergent compositions often contain a significant amount of pigment and filler and little or no water while liquid compositions generally contain no pigment or filler but may contain a significant amount of water, e.g., at least about 20 wt. % based on the weight of the composition, optionally together with other compatible compounds liquid at room temperature, such as glycerin, in which the active soap or synthetic detergent component is soluble.

The zinc compound and water-soluble zinc-complexing polyamine in complexed or uncomplexed form, may be added to the soap or detergent composition at any point in the conventional manufacture of these products. For example in the production of solid soap bars under the invention, soap chips may be weighed into a mixer, the complexed or uncomplexed zinc compound and polyamine of the invention, and the contemplated compatible adjuvants, if any, added thereto, and the total mixed for a long enough period to achieve uniformity of the mix. After mixing, the composition can be formed into framed or milled soap bars in accordance with the general procedure of the soap making art.

The following example further illustrates the invention.

EXAMPLE

To a sample of chips of a commercially available soap base composed of a mixture of sodium salts of about 80 wt. % of tallow fatty acids and about 20 wt. % of coconut oil and/or palm kernel oil fatty acids being masticated in a mixing machine at a temperature of about 25° C. are added 0.75 wt. % of titanium dioxide, 0.01 wt. % of tetrasodium ethylenediamine tetraacetic acid (EDTA), 2.50 wt. % of glycerin, 0.5 wt. % of fragrance, 1–2 wt. % of deionized water, 5 wt. % of SACHTOTEC zinc oxide and 1.0 wt. % of a polyethyleneimine having a weight average molecular weight of about 75,000 and sold by BASF under the trademark "Polymin P", all based on the total weight of the composition. The soap base constitutes about 88–89 wt. % of the total composition. Mastication is continued until a uniform appearing plastic mass is obtained.

The soap composition of the foregoing example is found to exert a substantially larger deodorant effect when used in ordinary washing operation than the same composition containing no zinc oxide or polyethyleneimine.

We claim:

1. A toilet deodorant soap or detergent composition comprising a surfactant and as a deodorizing component, either 1) in uncomplexed form, a water-insoluble zinc compound and a water-soluble zinc-complexing polyamine which is a polyalkyleneamine or a basic aminoacid polymer; or 2) a water-soluble complex of said water-insoluble zinc compound and said water-soluble zinc-complexing polyamine, said uncomplexed or complexed zinc compound and polyamine each being present in a relative amount of about 0.1 to 15 parts by weight, with said uncomplexed zinc compound and polyamine forming a water-soluble complex in the presence of at least about 12 parts by weight of water, and said deodorizing component in uncomplexed or complexed form being present in the composition in an amount of about 1 to 25 wt. % based on the weight of total surfactant.

2. The composition of claim 1 wherein said zinc compound is zinc oxide.

3. The composition of claim 2 wherein said zinc oxide present in uncomplexed form or that reacting to form said complex has a submicron primary particle size.

4. The composition of claim 1 wherein said polyamine is a polyalkyleneamine having a weight average molecular weight in the range of about 800 to 1,000,000.

5. The composition of claim 4 wherein said polyalkyleneamine is a polyalkyleneimine having the formula

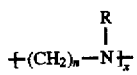

where R is a hydrogen, $C_1$–$C_3$ alkyl, or

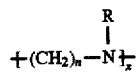

substituent, n is an integer in the range of 2–6, and x has a value such that weight average molecular weight of said polyalkyleneimine is within said range.

6. The composition of claim 1 wherein said polyamine is an aminoacid polymer having a weight average molecular weight in the range of about 1500 to 70,000.

7. The composition of claim 6 wherein said polymer is polyarginine, polylysine or polyhistidine.

8. The composition of claim 1 also containing an acidic reagent such that an aqueous solution of said complex has a pH in the range of about 6 to 10.

9. The composition of claim 1 wherein said surfactant is a soap.

10. The composition of claim 10 in the form of a solid bar.

11. The composition of claim 1 wherein said surfactant is a synthetic detergent.

12. The composition of claim 1 wherein said amount of deodorizing component is about 5 to 15 wt. %.

13. A method for making a toilet deodorant soap or detergent composition comprising blending a surfactant with about 0.1 to 15 parts by weight of zinc oxide composed of agglomerated submicron particles having an agglomerated size of about 1 to 10 microns, and about 0.1 to 15 parts by weight of a water-soluble zinc-complexing polyamine which is a polyalkyleneamine or a basic aminoacid polymer, said zinc oxide and polyamine forming a water-soluble complex in the presence of at least about 12 parts by weight of water, and the total of said zinc-oxide and polyamine being about 1 to 25 wt. % based on the weight of total surfactant.

14. A method of making a toilet deodorant soap or detergent composition comprising dissolving in an aqueous medium about 0.1 to 15 parts by weight of a water-soluble zinc-complexing polyamine which is a polyalkyleneamine or a basic aminoacid polymer, adding about 0.1 to 15 parts by weight of a water-insoluble zinc compound in powder form to the aqueous solution to form a water soluble zinc-polyamine complex which dissolves in the solution, adding an acid reagent to adjust the pH of the solution to between about 6 and 10, and blending the solution with a surfactant, said zinc-polyamine complex being present in an amount of about 1 to 25 wt. % based on the weight of total surfactant.

15. The method of claim 14 wherein said zinc compound is zinc oxide.

16. The method of claim 15 wherein said zinc oxide is composed of agglomerated submicron primary particle size particles having an agglomerated size of about 1 to 10 microns.

17. A method comprising washing the human body with the composition of claim 1.

* * * * *